US009967001B2

(12) United States Patent
Biederman (10) Patent No.: US 9,967,001 B2
(45) Date of Patent: May 8, 2018

(54) SYSTEMS AND METHODS FOR PASSIVE RADIO ENABLED POWER GATING FOR A BODY MOUNTABLE DEVICE (71) Applicant: Verily Life Sciences LLC, Mountain View, CA (US)

(72) Inventor: William Biederman, Oakland, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days. days.

(21) Appl. No.: 15/218,587

(22) Filed: Jul. 25, 2016

(65) Prior Publication Data

US 2018/0026678 A1    Jan. 25, 2018

(51) Int. Cl.
*H04B 5/00* (2006.01)
*H04W 52/02* (2009.01)
*A61B 5/145* (2006.01)
*A61B 5/00* (2006.01)

(52) U.S. Cl.
CPC ....... *H04B 5/0037* (2013.01); *A61B 5/14532* (2013.01); *A61B 5/6801* (2013.01); *H04W 52/0235* (2013.01); *A61B 2560/0214* (2013.01)

(58) Field of Classification Search
CPC combination set(s) only.
See application file for complete search history.

(56) References Cited

U.S. PATENT DOCUMENTS

| 8,947,041 | B2 * | 2/2015 | Cook | G06K 7/0008 |
| | | | | 320/108 |
| 9,110,897 | B2 * | 8/2015 | Park | A61B 5/002 |
| 2008/0116847 | A1 | 5/2008 | Loke | |
| 2010/0148723 | A1 * | 6/2010 | Cook | G06K 7/0008 |
| | | | | 320/108 |
| 2010/0292556 | A1 | 11/2010 | Golden | |
| 2011/0022411 | A1 | 1/2011 | Hjelm | |
| 2012/0028575 | A1 | 2/2012 | Chen et al. | |

(Continued)

FOREIGN PATENT DOCUMENTS

WO    2013063634    5/2013

OTHER PUBLICATIONS

Antonio J. Jara, Pablo Lopez, David Fernandez, Miguel A. Zamora, Benito Ubeda and Antonio F. Skarmeta , Communication Protocol for Enabling Continuous Monitoring of Elderly People through Near Field Communications, Interact. Comput. (2013) doi: 10.1093/iwc/iwt030 First published online: May 15, 2013.

(Continued)

*Primary Examiner* — Junpeng Chen
(74) *Attorney, Agent, or Firm* — Kilpatrick Townsend & Stockton LLP (57) ABSTRACT Systems and methods for passive radio enabled power gating for a body mountable device are disclosed. In one embodiment, a system for power gating includes: a power supply; a Near Field Communication (NFC) antenna to receive NFC signals; a Radio Frequency (RF) rectifier electrically coupled to the NFC antenna to generate a current based on a signal received from the NFC antenna; and an electronic switch coupled between the power supply and a sensor, wherein the RF rectifier is further coupled to the switch to apply the current to the switch to change a state of the switch.

22 Claims, 4 Drawing Sheets

(56) References Cited

U.S. PATENT DOCUMENTS

2014/0313052 A1\* 10/2014 Yarger .................. G06F 19/345
340/870.02
2015/0018643 A1 1/2015 Cole et al.
2015/0075770 A1\* 3/2015 Fripp .................. E21B 43/1185
166/65.1
2015/0343144 A1\* 12/2015 Altschul ................ A61K 45/06
604/503

OTHER PUBLICATIONS

International Application No. PCT/US2017/039380 , "International Search Report and Written Opinion", Sep. 7, 2017, 11 pages.

\* cited by examiner

SYSTEMS AND METHODS FOR PASSIVE RADIO ENABLED POWER GATING FOR A BODY MOUNTABLE DEVICE

BACKGROUND

Single use wearable sensors are becoming more popular. For many such sensors the period of time the sensor is worn by the user is a relatively small percentage of the lifetime of the sensor. For example, these sensors may comprise active components, e.g., a processor, memory, sensor, etc., which are powered by an onboard battery. However, one or more of these components may consume energy when the device is technically "off." For example, in some devices the processor must remain in a "low power" mode to detect whether the user has pressed the "on" button. However, storage and shipment prior to use may take many months. Thus, a significant portion of the total battery capacity may be consumed during storage prior to activation by the end user.

SUMMARY

In one embodiment, a system of the present disclosure may comprise: a power supply; a Near Field Communication (NFC) antenna to receive NFC signals; a Radio Frequency (RF) rectifier electrically coupled to the NFC antenna to generate a current based on a signal received from the NFC antenna; and an electronic switch coupled between the power supply and a sensor, wherein the RF rectifier is further coupled to the switch to apply the current to the switch to change a state of the switch.

Another embodiment of the present disclosure may comprise: receiving a Near Field Communication (NFC) signal using a NFC antenna; converting the NFC signal to a current; and applying the current to a switch positioned to interrupt current flow between a power supply and a load, the switch opened or closed by the current.

In one embodiment, a system of the present disclosure may comprise: a single use wearable glucose sensor comprising: a power supply; a Near Field Communication (NFC) antenna for receiving NFC signals; a Radio Frequency (RF) rectifier electrically coupled to the NFC antenna to generate a current based on a signal received from the NFC antenna; a blood glucose sensor; a processor coupled to the blood glucose sensor, the processor to: store sensor data received from the blood glucose sensor; transmit the sensor data to a remote device using the NFC antenna; and an electronic switch coupled between the power supply and the processor, wherein the RF rectifier is further coupled to the switch to apply the current to the switch to provide power from the power supply to the processor.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

A full and enabling disclosure is set forth more particularly in the remainder of the specification. The specification makes reference to the following appended figures.

DETAILED DESCRIPTION

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of Passive Radio Enabled Power Gating for a Body Mountable Device One illustrative embodiment of the present disclosure comprises a single use analyte sensor. For example, one such device may comprise a single use glucose sensing patch. Such a patch may be worn by the user for a predetermined time and configured to measure the user's blood sugar during that time and then disposed. The illustrative glucose sensing patch comprises active components, e.g., a processor, memory, sensor, etc., which are powered by an onboard battery. The illustrative glucose sensing patch prevents these active components from consuming energy until the device is in use by gating the power supply with a passive radio power gate utilizing Near Field Communication (NFC).

In the illustrative embodiment, the passive radio power gate comprises an NFC antenna configured to receive NFC signals from a device, e.g., a mobile device. These NFC signals are provided to an RF rectifier, which converts the NFC signals to current and/or voltage. This current is then used to control a switch, such as a transistor (e.g., a BJT or MOSFET), a relay, an electronically controlled switch, or other switching circuit. The switch closes, providing current from a power supply, such as a battery, to the active electronic components on the patch (e.g., a processor, memory, and sensor).

Once the switch is closed and the active components are powered, the sensor measures glucose (or some other analyte). The processor records these measurements in a memory. After a predetermined period of time, e.g., one day, one week, or two weeks, etc. the switch is reopened (e.g., automatically, by the processor, or by the user using an NFC enabled device), thus cutting power to active components. This preserves the remaining power in the battery, while the recorded data remains stored.

At some point after the predetermined time period the user may extract data from the patch. For example, the user may reactivate the patch by using an NFC enabled device to re-close the switch, powering the active components. The processor may then transmit data to a device (e.g., a mobile device) using an antenna configured to transmit data using known protocols, e.g., Wi-Fi or Bluetooth. Alternatively, the processor may transmit the stored data to the user's device using NFC, e.g., the processor may transmit data using the same NFC antenna used to activate and reactivate the patch. The user or a medical professional may then be able to review the transmitted data on a separate device (e.g., a mobile device or laptop or desktop computer system) or upload the data to a remote server accessible via a network, e.g., the Internet.

Further, the illustrative embodiment may provide methods for communicating with the patch, e.g., the glucose sensing patch during manufacture and shipping. For example, the patch may comprise a specific NFC signature, which is used for tracking and inventory management. Alternatively, the patch may comprise a diagnostic mode in which information about the patch, e.g., battery charge level, memory capacity, or other information may be measured by the processor and transmitted to a device using NFC. In such a diagnostic mode the patch may be activated for a limited period, e.g., while performing diagnostics, in order to preserve battery life for when the patch is worn by a user.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

Figure 1A:
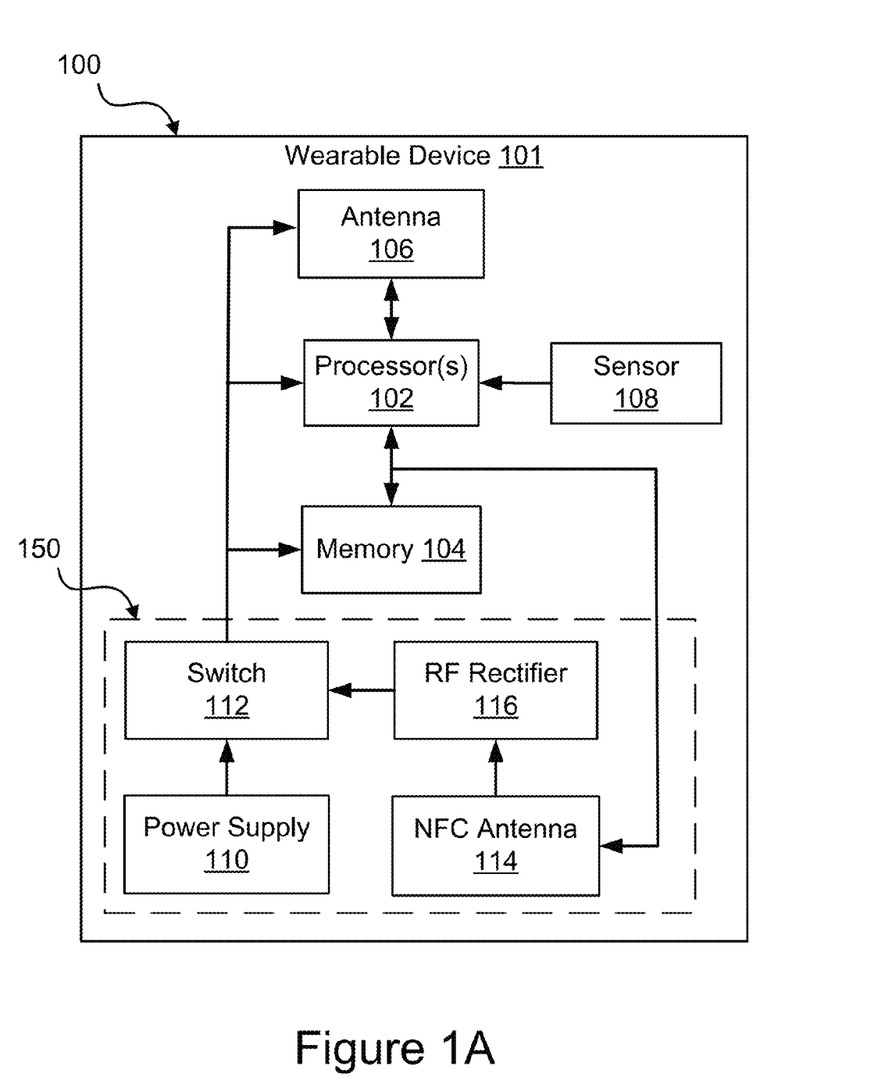
FIG. 1A shows an illustrative system for passive radio enabled power gating for a body mountable device according to one embodiment of the present disclosure.

Illustrative Systems for Passive Radio Enabled Power Gating for a Body Mountable Device FIG. 1A shows an illustrative system 100 for passive radio enabled power gating for a body mountable device according to one embodiment. The system 100 comprises wearable device 101, which may comprise a wearable analyte sensor, e.g., a wearable glucose sensor, hydration sensor, oxygen sensor, or other type of sensor, e.g., a temperature sensor, motion sensor, blood pressure sensor, heart rate sensor, metabolic sensor, or any other type of sensor known in the art. In one embodiment, wearable device 101 comprises a wearable patch comprising each of the components shown in FIG. 1A.

The wearable device 101 comprises a plurality of components that may comprise an active mode, e.g., a mode in which the device must receive power to operate. These active components comprise, e.g., processor(s) 102, memory 104, antenna 106, and sensor 108. In some embodiments, these components are not all active components, e.g., in some embodiments, sensor 108 and memory 104 may comprise both active and passive modes. Alternatively, in some embodiments, one or more of these components may comprise a passive component, e.g., sensor 108 may comprise a component that does not have an active mode.

Turning to processor 102, processor 102 comprises one or more of a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Processor 102 is in communication with memory 104. Memory 104 can comprise any suitable tangible (and non-transitory) computer-readable medium such as RAM, ROM, EEPROM, or the like, and may embody program components that configure operation of the computing device. Memory 104 may further comprise storage for processor 102 to store data, e.g., data received from a network interface or sensor 108. Memory 104 may comprise a static memory that can store data while in an unpowered state.

Antenna 106 represents one or more of any components that facilitate a network connection. Examples include, but are not limited to, wired interfaces such as Ethernet, USB, IEEE 1394, and/or wireless interfaces such as IEEE 802.11, Bluetooth, or radio interfaces for accessing cellular telephone networks (e.g., transceiver/antenna for accessing a CDMA, GSM, UMTS, or other mobile communications network(s)). Thus, antenna 106 enables processor 102 to transmit or receive data from a remote device.

Sensor 108 comprises a sensor configured to measure information about a user, e.g., an analyte sensor, e.g., a wearable glucose sensor, hydration sensor, oxygen sensor, or other type of sensor, e.g., a temperature sensor, motion sensor, blood pressure sensor, heart rate sensor, metabolic sensor, or any other type of sensor known in the art. In some embodiments, sensor 108 may comprise an active sensor, a passive sensor, or a sensor with both active and passive modes.

As shown in FIG. 1A wearable device 101 further comprises a passive radio gated power supply 150. The passive radio gated power supply 150 comprises a power supply 110, a switch 112, a Near Field Communication (NFC) antenna 114, and an RF Rectifier 116.

Power supply 110 comprises a source of power, e.g., an onboard power source such as a battery, e.g., a rechargeable or non-rechargeable battery, for example, an alkaline battery, aluminum-air battery, aluminum-ion battery, dry cell, lithium battery, magnesium battery, mercury battery, nickel oxyhydroxide battery, lead-acid battery, lithium air battery, lithium ion battery, magnesium ion battery, nickel cadmium battery, sodium ion battery, or any other type of battery known in the art. In some embodiments, power supply 110 may comprise an external power supply, e.g., a remote DC power supply coupled to wearable device 101 to power one or more components during or after manufacture, e.g., for testing, diagnostics, or charging.

Switch 112 comprises a switch configured to interrupt the flow of current from power supply 112 to one or more of the active components of wearable device 101. For example, in some embodiments, switch 112 may comprise a transistor (e.g., a BJT or MOSFET), a relay, an electronically controlled switch, an op-amp circuit, or other switching circuit, e.g., a solid-state or non-solid state circuit configured to interrupt the flow of current from a power source to a load. Further, after switch 112 is closed it may be configured to automatically reopen after a predetermined period of time, e.g., one week or two weeks. Further, in some embodiments, switch 112 may be controlled by processor(s) 102 to be opened after the predetermined period of time, thus cutting the flow of current from power supply 110 to the active components. In still other embodiments, the user may reopen the switch 112 using an NFC enabled device as described in further detail below.

NFC antenna 114 comprises an interface configured to transmit and receive NFC signals. For example, NFC antenna 114 may comprise an NFC controller IC configured to receive/generate NFC signals, which are transmitted with an appropriately sized antenna. Further, in some embodiments discussed in further detail below, NFC antenna 114 and antenna 106 may be integrated into a single component.

RF rectifier 116 is a component configured to receive NFC signals from NFC antenna 112 and convert those signals to current. For example, RF rectifier 116 may comprise an RF to DC converter that takes energy received from Radio Frequency (RF) signals and converts that energy to DC current. The RF rectifier 116 is coupled to the switch 112, such that the current from the RF rectifier 116 is used to either open or close switch 112. In some embodiments, the RF rectifier 116 directly controls switch 112. In other embodiments, rather than directly controlling switch 112, the RF rectifier 116 will indirectly control switch 112. In such an embodiment, RF rectifier 116 controls circuitry and or logic that demodulates communication signals received from antenna 106 or NFC antenna 114, or another wired or wireless communication interface, e.g., a serial peripheral interface (SPI). Based on these signals the circuitry may then control the switch 112 to provide power from power supply 110 to the active components in the wearable device 101. For example, in one embodiment, RF rectifier 116 may provide power to circuitry (e.g., analog or digital circuitry) configured to interpret NFC signals received by NCF antenna 114. This circuitry may then control switch 112 based on the content of the NFC signals. For example, an NFC signal may comprise an indication to activate. Based on this signal the circuitry may provide power to all active components in wearable device 101. In another embodiment, the NFC signal may comprise an indication to transmit. In such an embodiment, the circuitry may provide power to components needed to transmit data stored in memory 104 using one or more of antenna 106 or NFC antenna 114.

Thus, in one embodiment, wearable device 101 may comprise a single use patch for sensing the user's blood sugar level. The single use patch may be manufactured and shipped with switch 112 open, such that none of the active components consume energy from power source 110 until the switch 112 is closed.

Figure 1B:
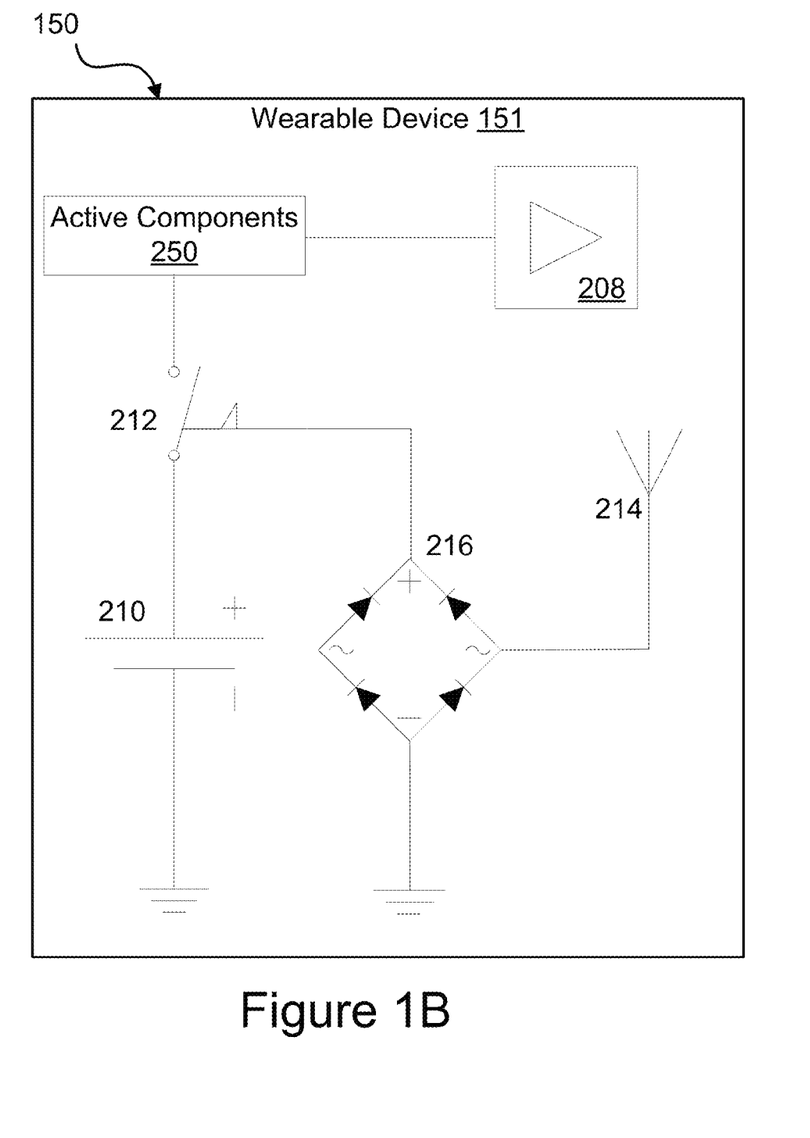
FIG. 1B shows another illustrative system for passive radio enabled power gating for a body mountable device according to one embodiment of the present disclosure.

FIG. 1B shows another illustrative system for passive radio enabled power gating for a body mountable device according to one embodiment of the present disclosure. FIG. 1B shows system 100, which comprises wearable device 151. Wearable device 151 comprises a wearable device of the same type described above with regard to FIG. 1A. As shown in FIG. 1B, wearable device 151 comprises sensor 208, power supply 210, switch, 212, NFC antenna 214, RF rectifier 216, and active components 250.

In operation, once the wearable device 151 is placed in position, e.g., mounted to the user, the user or a medical professional may activate the wearable device 151 using an NFC enabled device, e.g., an NFC enabled smartphone. The user may place the NFC enabled smartphone close to the wearable device 151 and activate NFC transmission. This NFC transmission is received by the NFC antenna 214. The NFC signals are used by RF rectifier 216 to generate a current. This current is provided to switch 212 and closes the switch, thus providing current from power supply 212 to active components 250, e.g., one or more processor(s) and a memory. In some embodiments, the RF rectifier 216 directly controls switch 212. In other embodiments, rather than directly controlling switch 212, the RF rectifier 216 will indirectly control switch 212. For example, in some embodiments, the RF rectifier 216 may provide power to analog or digital logic that interprets (e.g., demodulates) NFC signals and controls the switch 212 based on the content of those signals. Once active, the processor may receive signals from sensor 208 and record those signals in the memory.

In such an embodiment, the processor may be configured to reopen switch 212 after a predetermined period of time. This predetermined period of time may comprise the operating life of the wearable device 151 (e.g., a predetermined number of days or weeks, e.g., fourteen days). At this point the active components 250 will stop consuming power from the power supply 210. In such an embodiment, the power supply 210 may comprise a battery that is specifically designed to provide power to the active components for only a relatively short period of time, e.g., the predetermined period. This may enable a relatively smaller, lighter, and cheaper battery to be used than would be required without passive radio enabled power gating.

Further, at some point after the switch 212 is reopened and wearable device 151 is deactivated, the user or a medical professional may download the sensor data stored in the memory. To do so, the user or the medical professional may reactivate the wearable device 151 using an NFC enabled device, e.g., an NFC enabled mobile device, such as a smartphone. These NFC signals may be used to close the switch 212, which then provides current to the active components.

Figure 2:
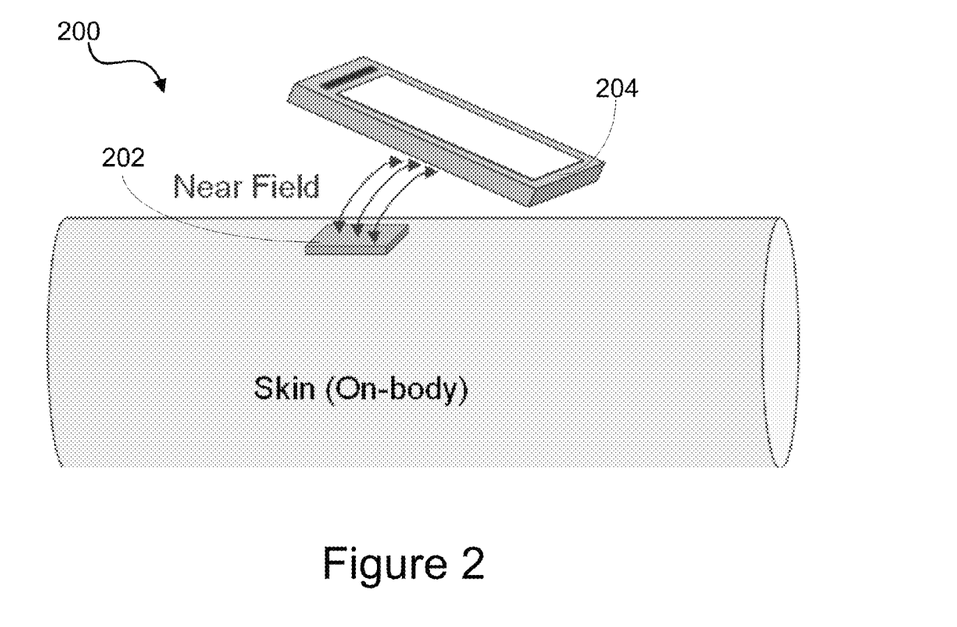
FIG. 2 shows another illustrative system for passive radio enabled power gating for a body mountable device according to another embodiment of the present disclosure.

In such an embodiment, the processor may enter a transmit mode, in which the processor transmits the data stored in the memory using NFC antenna 214. For example, the processor may automatically enter a transmit mode. The processor may then transmit the data stored in the memory to that remote device. FIG. 2 shows an illustrative system 200 for passive radio enabled power gating for a body mountable device according to one embodiment. As shown in FIG. 2, the system 200 comprises a single use patch 202 for sensing and recording data about the user (e.g., pulse, temperature, or blood sugar level). As discussed above, the single use patch may be manufactured and shipped with a switch interrupting the flow of current from its power supply to any active component, thus ensuring that battery power is not used during transportation or storage.

As shown in FIG. 2, once the wearable device 202 is placed in position, e.g., mounted to the user, the user or a medical professional may activate the wearable device 202 using an NFC enabled device 204. In some embodiments, NFC enabled device 204 may comprise a mobile device such as an NFC enabled smartphone or tablet, or some other computing device comprising NFC functionality. As discussed above, these NFC signals may be used to provide power to a switch to close the switch and allow current to flow from a power source to the active components of the wearable device 202.

As discussed above, the processor may control the switch such that it is reopened after a predetermined period of time, e.g., the operating life of the wearable device 202. At this point the active components will stop consuming power from power supply. In such an embodiment, the power supply may comprise a battery that is specifically designed to provide power to the active components for only a relatively short period of time, e.g., the predetermined period.

Further, as shown in FIG. 2, at some point after the switch is reopened and wearable device 202 is deactivated, the user or a medical professional may download the sensor data stored in a memory. The user or the medical professional may reactivate the wearable device using an NFC enabled device to close the switch and thus allow current to flow from the battery to the active components.

In such an embodiment, the wearable device 202 may enter a transmit mode, in which the processor transmits the data stored in a memory. This data may be transmitted using a second transmission means, e.g., a network interface such as a Wi-Fi or Bluetooth interface. Alternatively, the wearable device may be configured to transmit the measured sensor data using the same NFC interface used to close the switch. Once the sensor data is transmitted it may be reviewed locally, e.g., on the NFC enabled device, or transmitted to a further remote device, e.g., uploaded to a remote server using an Internet connection.

Figure 3:
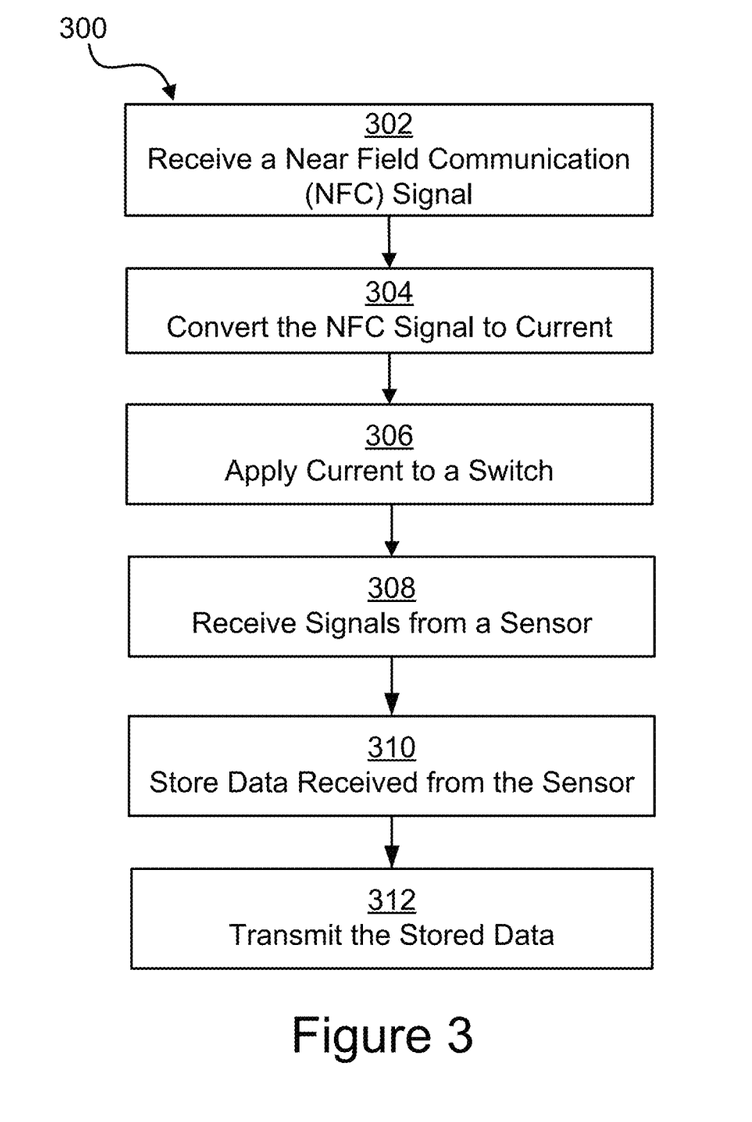
FIG. 3 is a flow chart for a method for passive radio enabled power gating for a body mountable device according to one embodiment of the present disclosure.

Illustrative Methods for Passive Radio Enabled Power Gating for a Body Mountable Device FIG. 3 is a flow chart for a method of passive radio enabled power gating for a body mountable device. In some embodiments, the steps in FIG. 3 may be implemented in program code executed by a processor. In some embodiments, these steps may be implemented by a group of processors. In some embodiments the steps shown in FIG. 3 may be performed in a different order. Alternatively, in some embodiments, one or more of the steps shown in FIG. 3 may be skipped, or additional steps not shown in FIG. 3 may be performed. The steps below are described with reference to components described above with regard to system 100 shown in FIG. 1A.

The method 300 begins at step 302 when wearable device 101 receives a Near Field Communication (NFC) signal using NFC antenna 114. The NFC signal may be received from a mobile device, e.g., a smartphone or tablet comprising NFC capability. Alternatively, the NFC signal may be received from a purpose built device configured to activate wearable device 101.

The method 300 continues to step 304 when RF rectifier 116 converts the NFC signal to current. RF rectifier may comprise an RF to DC converter configured to convert NFC signals received from antenna 114 to DC current.

Next at step 306 the RF rectifier 116 applies current to switch 112. In one embodiment, the RF rectifier 116 directly controls switch 112. In such an embodiment, switch 112 is electrically coupled to RF rectifier 116 in a configuration such that current from RF rectifier 116 is configured to close switch 112 and thus provide current to one or more active components on wearable device 101, e.g., processor 102, memory 104, and sensor 108. In some embodiments, RF rectifier 116 may indirectly control switch 112, for example, by controlling analog or digital circuitry to apply current to switch 112. In one such embodiment, the analog or digital circuitry may be configured to demodulate NFC signals received from NFC antenna 114 and determine data contained in those signals. The circuitry may control switch 112 based on those signals, e.g., control the switch 112 to power all active components or control the switch 112 to power only components necessary to transmit data stored in memory 104 to a remote device. Further, switch 112 is configured to be reopened, for example, automatically after a predetermined period of time, after receipt of a control signal from processor 102, or after receipt of additional current from RF rectifier 116 (for example, the user may use a NFC enabled device to open switch 112 to deactivate wearable device 101).

Then at step 308 processor 102 receives signals from sensor 108. The sensor 108 is configured to measure information about a user, e.g., sensor 108 may comprise an analyte sensor, e.g., a wearable glucose sensor, hydration sensor, oxygen sensor, or other type of sensor, e.g., a temperature sensor, motion sensor, blood pressure sensor, heart rate sensor, metabolic sensor, or any other type of sensor known in the art. In some embodiments, sensor 108 may comprise an active sensor, a passive sensor, or a sensor with both active and passive modes.

Next, at step 310 the processor 102 stores data received from the sensor 108 in memory 104. Memory 104 may comprise a static memory, e.g., flash or EEPROM, configured to store the sensor data received from processor 102 after switch 112 is reopened and power is no longer provided to the active components in wearable device 101.

Then at step 312 the processor transmits the stored data to a remote device. In such an embodiment, the processor 102 may enter a transmit mode, in which the processor 102 transmits the data stored in memory 104 using antenna 106. Alternatively, in some embodiments, processor 102 may transmit data stored in memory 104 using an NFC protocol and NFC antenna 114.

Advantages of Passive Radio Enabled Power Gating for a Body Mountable Device

There are numerous advantages of passive radio enabled power gating for a body mountable device. For example, one advantage is that a device implementing passive radio enabled power gating may use substantially less energy over the course of its lifetime because no energy is consumed during shipping or storage. This may allow smaller batteries to be used in such devices. These smaller batteries may be smaller, lighter, and cheaper, making a corresponding device using the battery, e.g., a single use wearable sensor, smaller, lighter, and cheaper. Further, embodiments of the present disclosure may enable a single use device to upload stored data using only a relatively small amount of energy. This makes such devices more effective and reliable, because there is less risk that the user will be unable to retrieve measured data at the end of the device's usable life.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor. The processor executes computer-executable program instructions stored in memory, such as executing one or more computer programs including a sensor sampling routine, selection routines, and other routines to perform the methods described above.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. A system for power gating for a wearable glucose sensor comprising:
    a power supply;
    a Near Field Communication (NFC) antenna to receive NFC signals;
    a Radio Frequency (RF) rectifier electrically coupled to the NFC antenna to generate a current based on a first signal received from the NFC antenna;
    a sensor terminal adapted to electrically couple to a sensor;
    a memory coupled to the sensor and configured to store data received from the sensor;
    an electronic switch coupled between the power supply and the sensor terminal to control electrical connection between the power supply in the sensor terminal, wherein the RF rectifier is further coupled to the electronic switch to apply the current to the electronic switch to change a state of the electronic switch; and
    a network interface coupled to the memory, the network interface activated by a second NFC signal and transmit data stored in the memory to a remote device.

2. The system of claim 1, wherein the electronic switch comprises one or more of: a transistor, a relay, or an electronically controlled switch.

3. The system of claim 1, wherein the power supply comprises a battery.

4. The system of claim 1, wherein the electronic switch is further coupled between the power supply and a processor.

5. The system of claim 4, wherein the processor is coupled to the sensor to receive sensor data from the sensor when the electronic switch is closed, and to the memory to store the sensor data in the memory.

6. The system of claim 5, wherein the processor is coupled to the NFC antenna to transmit data using the NFC antenna.

7. The system of claim 5, further comprising a second antenna and wherein the processor is coupled to the second antenna to transmit data using the second antenna, and wherein the second antenna is configured to transmit data using a different protocol than the NFC antenna.

8. The system of claim 4, wherein the sensor comprises a glucose sensor.

9. The system of claim 1, further comprising a processor coupled to:
    the electronic switch to receive a second current from the power supply when the electronic switch is closed,
    the sensor to receive one or more sensor signals from the sensor, and
    the NFC antenna to transmit stored data using the NFC antenna.

10. A method for power gating comprising:
    receiving a Near Field Communication (NFC) signal using a NFC antenna;

converting the NFC signal to a current;
applying the current to an electronic switch positioned to interrupt current flow between a power supply and a load, the electronic switch opened or closed by the current;
activating a sensor to measure blood glucose and transmit sensor data associated with blood glucose;
storing the sensor data in a memory;
activating a network interface based in part on a second NFC signal; and
transmitting stored sensor data to a remote device using the network interface.

11. The method of claim 10, wherein the electronic switch comprises one or more of: a transistor, a relay, or an electronically controlled switch.

12. The method of claim 10, wherein the power supply comprises a battery.

13. The method of claim 10, wherein the load comprises a processor and a sensor.

14. The method of claim 13, further comprising, when the electronic switch is closed:
receiving, from the sensor, signals comprising sensor data; and
storing the sensor data in a memory.

15. The method of claim 14, wherein the sensor comprises a glucose sensor.

16. The method of claim 14, further comprising transmitting data associated with the sensor data to a remote device.

17. The method of claim 16, wherein the data is transmitted using the NFC antenna.

18. The method of claim 16, wherein the data is transmitted using a second antenna, and wherein the second antenna is configured to transmit data using a different protocol than the NFC antenna.

19. The method of claim 10, further comprising transmitting stored data using the NFC antenna.

20. A wearable glucose sensor comprising:
a power supply;
a Near Field Communication (NFC) antenna for receiving NFC signals;
a Radio Frequency (RF) rectifier electrically coupled to the NFC antenna to generate a current based on a first signal received from the NFC antenna;
a blood glucose sensor;
a processor coupled to the blood glucose sensor, the processor to:
store sensor data received from the blood glucose sensor;
upon receipt of a second signal received from the NFC antenna, transmit the sensor data to a remote device using a network interface; and
an electronic switch coupled between the power supply and the processor, wherein the RF rectifier is further coupled to the electronic switch to apply the current to the electronic switch to provide power from the power supply to the processor.

21. The wearable glucose sensor of claim 20, wherein the electronic switch comprises one or more of: a transistor, a relay, or an electronically controlled switch.

22. The wearable glucose sensor of claim 20, wherein the remote device comprises one or more of: a smartphone, a tablet, or a laptop computer.

* * * * *